(12) United States Patent
Butt et al.

(10) Patent No.: US 7,016,027 B2
(45) Date of Patent: Mar. 21, 2006

(54) SYSTEM AND METHOD FOR QUANTIFYING ERRORS IN AN ALTERNATING PHASE SHIFT MASK

(75) Inventors: Shahid Butt, Ossining, NY (US); Shoaib Zaidi, Poughkeepsie, NY (US)

(73) Assignee: Infineon Technologies AG, Munich (DE)

( * ) Notice: Subject to any disclaimer, the term of this patent is extended or adjusted under 35 U.S.C. 154(b) by 288 days.

(21) Appl. No.: 10/431,368

(22) Filed: May 8, 2003
(Under 37 CFR 1.47)

(65) Prior Publication Data

US 2004/0223145 A1 Nov. 11, 2004

(51) Int. Cl.
*G01N 21/00* (2006.01)
(52) U.S. Cl. .................................... 356/237.1
(58) Field of Classification Search ............. 356/239.1, 356/237.2, 237.3, 237.4, 237.5, 432, 433; 250/559.41, 559.39; 430/30
See application file for complete search history.

(56) References Cited

U.S. PATENT DOCUMENTS

| | | | |
|---|---|---|---|
| 5,539,514 A * | 7/1996 | Shishido et al. ......... 356/237.4 |
| 5,576,829 A | 11/1996 | Shiraishi et al. |
| 5,963,329 A | 10/1999 | Conrad et al. |
| 6,007,950 A | 12/1999 | Lin |
| 6,057,064 A | 5/2000 | Lin |
| 6,096,457 A | 8/2000 | Pierrat |
| 6,134,008 A | 10/2000 | Nakao |
| 6,183,916 B1 | 2/2001 | Kuo et al. |
| 6,327,033 B1 * | 12/2001 | Ferguson et al. ........... 356/394 |
| 6,428,936 B1 * | 8/2002 | Schenker ...................... 430/5 |
| 6,428,938 B1 | 8/2002 | Lin et al. |
| 6,466,315 B1 * | 10/2002 | Karpol et al. ............ 356/237.4 |
| 6,696,208 B1 * | 2/2004 | Czech et al. ................... 430/30 |
| 6,820,321 B1 * | 11/2004 | Harding ..................... 29/602.1 |
| 2002/0058348 A1 | 5/2002 | Lee |
| 2002/0197542 A1 * | 12/2002 | Lai et al. ....................... 430/30 |
| 2003/0054268 A1 * | 3/2003 | Czech et al. ................... 430/30 |
| 2004/0018435 A1 * | 1/2004 | Kim .............................. 430/5 |
| 2004/0105577 A1 * | 6/2004 | Wu et al. .................... 382/144 |
| 2004/0180278 A1 * | 9/2004 | Sato et al. ..................... 430/30 |
| 2004/0212796 A1 * | 10/2004 | Adel et al. ............... 356/237.1 |

FOREIGN PATENT DOCUMENTS

| | | |
|---|---|---|
| EP | 0628806 | 12/1994 |
| WO | WO 02/099533 | 12/2002 |
| WO | WO 03/026000 | 3/2003 |

* cited by examiner

OTHER PUBLICATIONS

R.A. Budd et al. Development and Application of a New Tool for Lithographic Mask Evaluation, the Stepper Equivalent Aerial Image Measurement System, AIMS, IBM J. Res. Develop. vol. 41 No. 1/2 Jan./Mar. 1997, 119-129.

*Primary Examiner*—Layla G. Lauchman
*Assistant Examiner*—Juan D. Valentin, II
(74) *Attorney, Agent, or Firm*—Edell, Shapiro & Finnan, LLC (57) ABSTRACT

A method and system for detecting the quality of an alternating phase shift mask having a number of 180-degree phase shift areas alternating with a number of 0-degree phase shift areas is disclosed. In operation, a light source which provides wavelength-adjustable incident lights illuminates the incident lights on the alternating phase shift mask. The light outputs from boundaries between the 0-degree phase shift areas and the 180-degree phase shift areas of the alternating phase shift mask are detected. Relation curves of the wavelength of the incident light and a light intensity of the boundaries are then calculated. Phase errors of the alternating phase shift mask can thus be measured from the relation curves.

14 Claims, 8 Drawing Sheets

SYSTEM AND METHOD FOR QUANTIFYING ERRORS IN AN ALTERNATING PHASE SHIFT MASK

BACKGROUND

1. Field of the Invention

The present invention generally relates to a system and method for detecting the quality of an alternating phase shift mask and, more particularly, to a system and method for detecting and quantifying errors in an alternating phase shift mask.

2. Background of the Invention

Figures 1A, 1B:
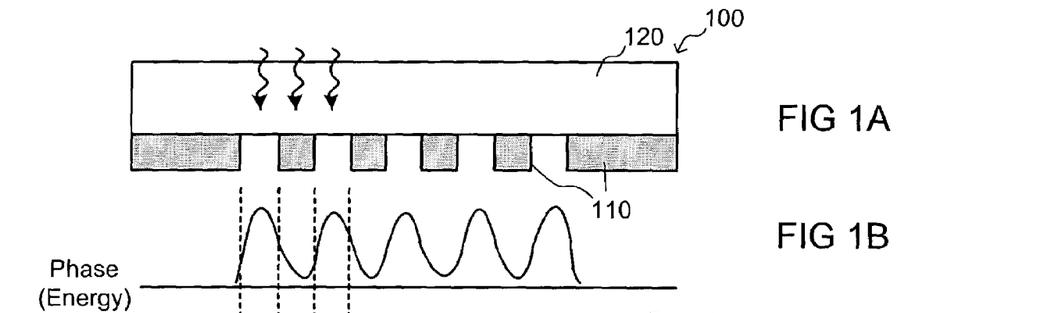

Photolithography is commonly utilized in the field of semiconductor manufacturing to form features (or patterns) on a wafer substrates. In one type of photolithography, known as "binary intensity mask" ("BIM") photolithography, a photoresist or mask formed with patterns composed of opaque areas (such as chrome) and transparent areas (such as quartz) is placed above a semiconductor layer where a pattern will be formed, such as an insulating layer or a conductive layer on a semiconductor substrate. As illustrated in FIG. 1, a mask 100, together with a substrate underlayer 10, is exposed to radiation light, which may include x-ray, ultraviolet rays or other rays. Projected light within a specific wavelength region passes through transparent areas 120 of the mask to the substrate underlayer 10, but is blocked by opaque areas of the mask 110. In this manner, the exposed areas of the underlayer 10 incident to the light can be removed in a subsequent developing process, leaving the unexposed areas to remain as features on the underlayer 10 (see FIG. 1D). Such developing steps are known as a "negative developing method". Alternatively, patterning can be performed by a "positive developing method", where the exposed areas of the underlayer 10 incident to the light remain, but unexposed areas are removed.

Sequentially, several deposition processes and etching processes are applied to the semiconductor substrate with the patterned underlayer to form electrodes and interconnection of semiconductor devices.

Figure 1C:
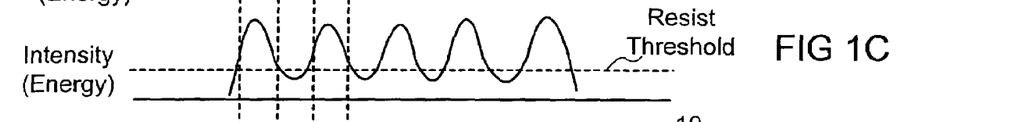
FIG. 1C is a light intensity distribution curve after the light passes through the BIM.
Figure 1D:
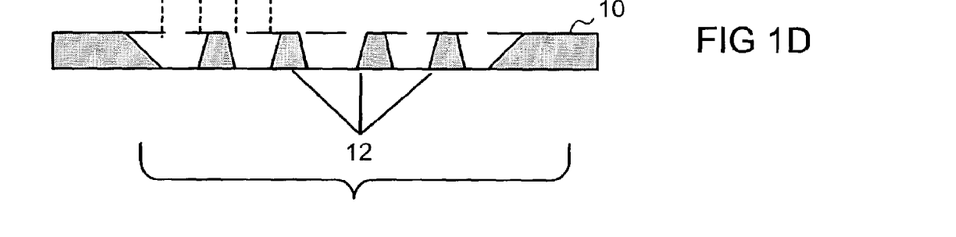
FIG. 1D shows the profiles developed on the underlayer of the IBM after the photolithography process is completed.

FIGS. 1B and 1C illustrate a phase energy distribution curve and a light intensity curve, respectively, at areas where light passes through transparent regions of mask 100. As shown in FIG. 1B, the phase, or energy of the light that is emitted from the transparent regions of the mask appears as approximately sinusoidal pattern. Although light is blocked at the opaque areas, the phase of the beam that is emitted at the edges of transparent areas will have a shift in phase. FIG. 1C illustrates the intensity of the emitted light beam, which roughly corresponds to the square of energy. As can be seen, the beam that is emitted from the transparent areas is dispersed at a reduced intensity at areas below the opaque areas.

As semiconductor devices become more highly integrated, it becomes increasingly important to improve photolithography techniques to form finer patterns on masks. As feature sizes and pitches shrink, however, the resolution of the projection optics begins to limit the quality of the mask pattern. Particularly, IC feature sizes have decreased into a subwavelength range, below 130 nm, which is smaller than the wavelength of light output from currently-used optical lithography equipment. Lithographers are now utilizing light with a wavelength of 193 nm for patterning critical layers of 100 nm-technology nodes.

As shown in FIGS. 1A–1D, which are representative of optics in the subwavelength range, there is significant light energy (i.e., intensity) even below the opaque areas (see FIG. 1C) because the transparent areas and the opaque areas are extremely close to each other. This "unwanted" energy results in light diffraction that significantly affects the quality of the mask profile, which ideally should be vertical, especially at the boundaries between the opaque areas 110 and the transparent quartz areas 120. When light diffraction occurs, the regions on the substrate 10 that should be dark receive diffracted light, thereby causing those regions to be blurred and not distinguishable. As shown in FIG. 1D, after mask development, the boundaries 12 of the pattern 11 are not vertical to the surface of the underlayer 10 because of the above-mentioned light diffraction effects. As a result, the quality and yield of semiconductor devices that are manufactured by this mask are poor.

With the increasing demand for manufacture of semiconductor devices in a subwavelength region, a number of "subwavelength" technologies have been introduced in the industry. Among them, phase-shift masks ("PSM"), which enable the clear regions of a mask to transmit light with a prescribed phase shift, have been introduced to control the printability of the mask.

Figure 2A:
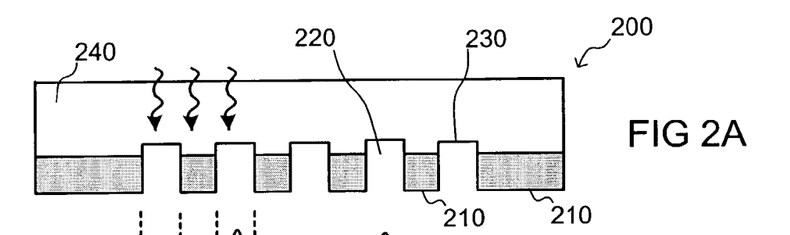

Phase shift lithography provides a method for reducing the effects of the above-described light diffraction. One type of PSM is called an alternating PSM (AltPSM), which is shown in FIGS. 2A–2D. As shown in FIG. 2A, an AltPSM 200 is manufactured by depositing an opaque material (such as chrome) on a transparent substrate, such as quartz 240, to form opaque chrome areas 210 on the quartz that are arranged alternatively with the transparent quartz areas 220 and 230. Then, alternating quartz areas (i.e., areas 230) are etched into the mask to form 180-degree-phase-shift quartz areas. Adjacent transparent quartz areas on the mask, which are separated by the opaque areas 210, are created such that the phase of the light incident upon one of the transparent areas (such as area 230) is shifted, or delayed by 180-degrees from that of light incident upon the adjacent transparent area 220.

Figures 2B, 2C:
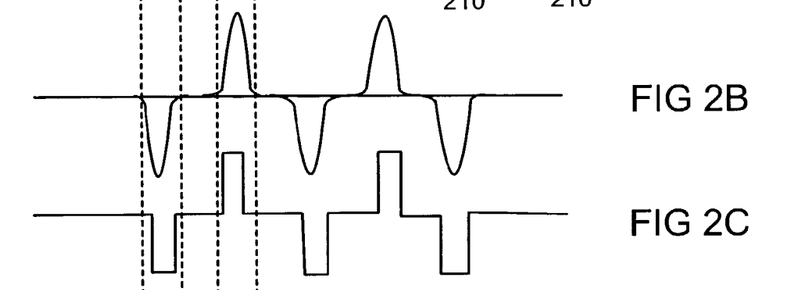
FIG. 2B is a phase distribution curve after a light passes through the AltPSM.
FIG. 2C is a transmission profile of the AltPSM showing that the AltPSM will yield frequency-doubled patterns on the wafer substrate.
Figure 2D:
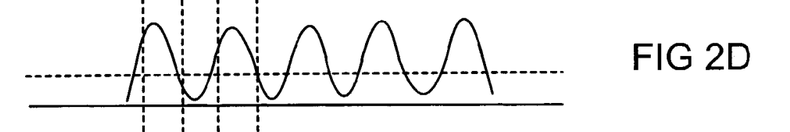
FIG. 2D is a light intensity distribution curve after the light passes through the AltPSM.
Figure 2E:
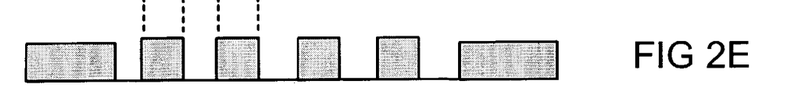
FIG. 2E shows the profiles developed on the underlayer of the AltPSM after the photolithography process is completed.

FIG. 2B illustrates that the light emitted from adjacent transparent quartz areas is characterized by a 180-degree phase shifting. By employing two adjacent transparent areas having respective phase shifts of 0 and 180-degrees, the light diffracted into the nominally dark regions between these adjacent transparent areas interfere destructively (to cancel out each other), such that the dark regions will remain dark. FIG. 2C is a transmission profile of the AltPSM, showing that the AltPSM will yield frequency-doubled patterns on the wafer substrate 10. FIG. 2D shows that the intensity of the energy decreases to 0 when the light passes through transitions of adjacent transparent quartz areas, thus resulting in sharp profiles on the underlayer 10. As shown in FIG. 2E, the underlayer 10 has vertical profiles 15, with a sharp and clear image contrast. The clear image contrast leads to a better resolution and better depth of focus.

As the lithographic k1 factor is reduced, the advantages associated with AltPSM increase the chances of obtaining a clear image contrast. In addition to frequency doubling, AltPSM also provides an added benefit of an improved process window and a reduced sensitivity to mask errors.

Although utilizing AltPSM is a powerful solution for improving the photolithographic technique in today's subwavelength industry, it is considered to be more demanding and expensive in comparison with use of a BIM. Particularly, an AltPSM must be evaluated for light intensity imbalance between shifted and unshifted space areas, and phase defect controllability. To maximize the benefit of using AltPSM, it is necessary that the unshifted areas and the 180-degree phase shift areas are perfectly balanced, both in transmission and in phase.

FIGS. 3A–3D are graphs that illustrate the impact of various errors by the diffraction pattern that can occur using an AltPSM. In each graph, at the boundaries between 0-degree and 180-degree phase shift areas, the numerical aperture ("NA") 0. These boundaries between the 0-degree and 180-degree phase shift are the locations of the zeroth order of the intensity of the light passing through the mask. These figures illustrate whether there are errors occurring at the zero point, i.e., the boundary between the 0-degree phase shift and the 180-degree phase shift, because it is where the phase error and the transmission error can occur. In other words, what determines errors can be detected by light diffraction at the zero point, i.e., at NA=0.

Figure 3A:
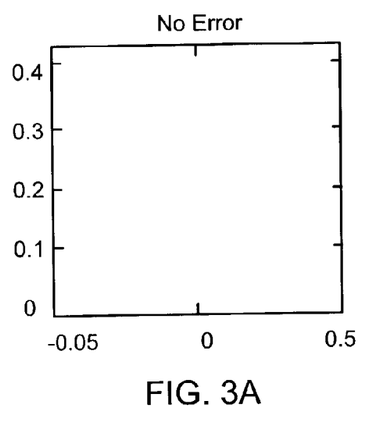
FIG. 3A is an ideal light diffraction pattern on the AltPSM, in which no error occurs at NA=0.

FIG. 3A shows an ideal diffraction pattern, where no error occurs at the zero point. In this figure, the light intensity at NA=0 is 0, indicating that light passing through the boundaries between the 0-degree phase shift and 180-degree phase shift areas are perfectly canceled out. Therefore, when applying this mask in the lithography process, the areas of the underlayer which correspond to the boundaries will leave sharp lines.

There are at least three types of errors that may influence the quality of the AltPSM. Generally, a phase error may exist if an incorrect material depth is obtained relative to the refractive index of the incident light (for example, if the etched transparent areas 230 in FIG. 2A are etched such that areas are too deep or too shallow). In this case, light diffraction occurs at the position NA=0 as a phase error, as shown in FIG. 3B.

A second kind of error that may occur in a PSM is known as a critical dimension ("CD") error. CD errors may exist if the critical dimensions of the semiconductor device (for example, a gate of the semiconductor device) is not carefully controlled. FIG. 3C shows that a light diffraction also occurs at the position NA=0 when there is a CD error.

A third type of error that may occur in a PSM is a transmission error. The occurrence of a transmission error may be attributed to a phase-shifted opening (such as an etched transparent quartz area 230 of FIG. 2), which is dependent upon etch roughness as well as electromagnetic scattering phenomena from the sidewalls of the etching opening. FIG. 3D shows there is a light diffraction at the position NA=0 when the transmission error occurs.

Figure 3B:
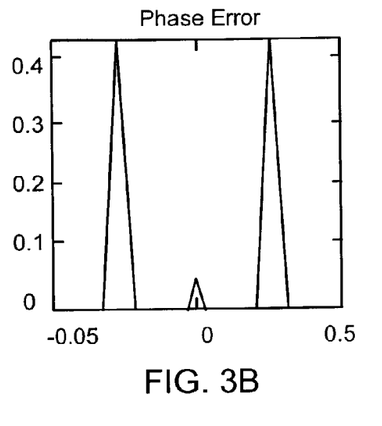
FIG. 3B is a light diffraction pattern on the AltPSM when a phase error occurs at NA=0.
Figure 3C:
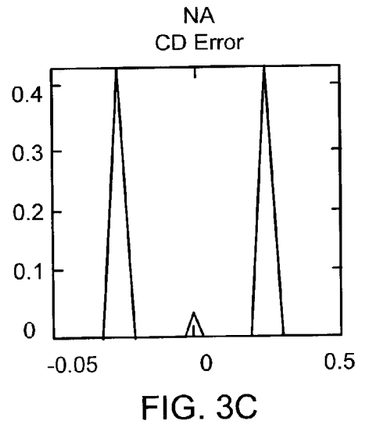
FIG. 3C is a light diffraction pattern on the AltPSM when a CD error occurs at NA=0.
Figure 3D:
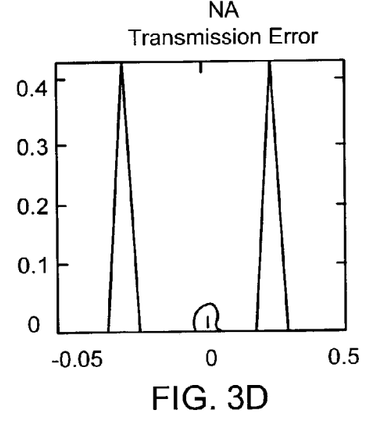
FIG. 3D is a light diffraction pattern on the AltPSM when a transmission error occurs at NA=0.

As shown in FIGS. 3B–3D, any imbalance in the transmission, phase or CD of the mask results in the presence of a DC component in FIGS. 2B–2D. Therefore, it is important to detect the DC component of the PSM to evaluate the quality of the mask.

There are a number of techniques for measuring CD error. For example, CD error can be detected by using a scanning electron microscope ("SEM"), looking down from the top of the mask. The CD error can be detected if there are unequal lines within two regions. However, it can be difficult and cumbersome to detect phase errors and transmission errors with a SEM and the results are often inaccurate.

As described above, since a phase shift is generated by etching into the quartz on the mask, there can be a significant amount of transmission imbalance between the 180-degree areas and the 0-degree areas due to scattering etching processes, etc. Several methods have been used to compensate for this, however, due to the non-linear behavior of transmission loss error, the compensation is generally non-uniform.

To date, the predominant method for characterizing transmission error and phase error has been to use tools such as the Aerial Image Measurement System, or "AIMS," which rapidly evaluates the exposure and depth-of-focus ("DOF") characteristics of masks before resist experiments are undertaken.

Figure 4:
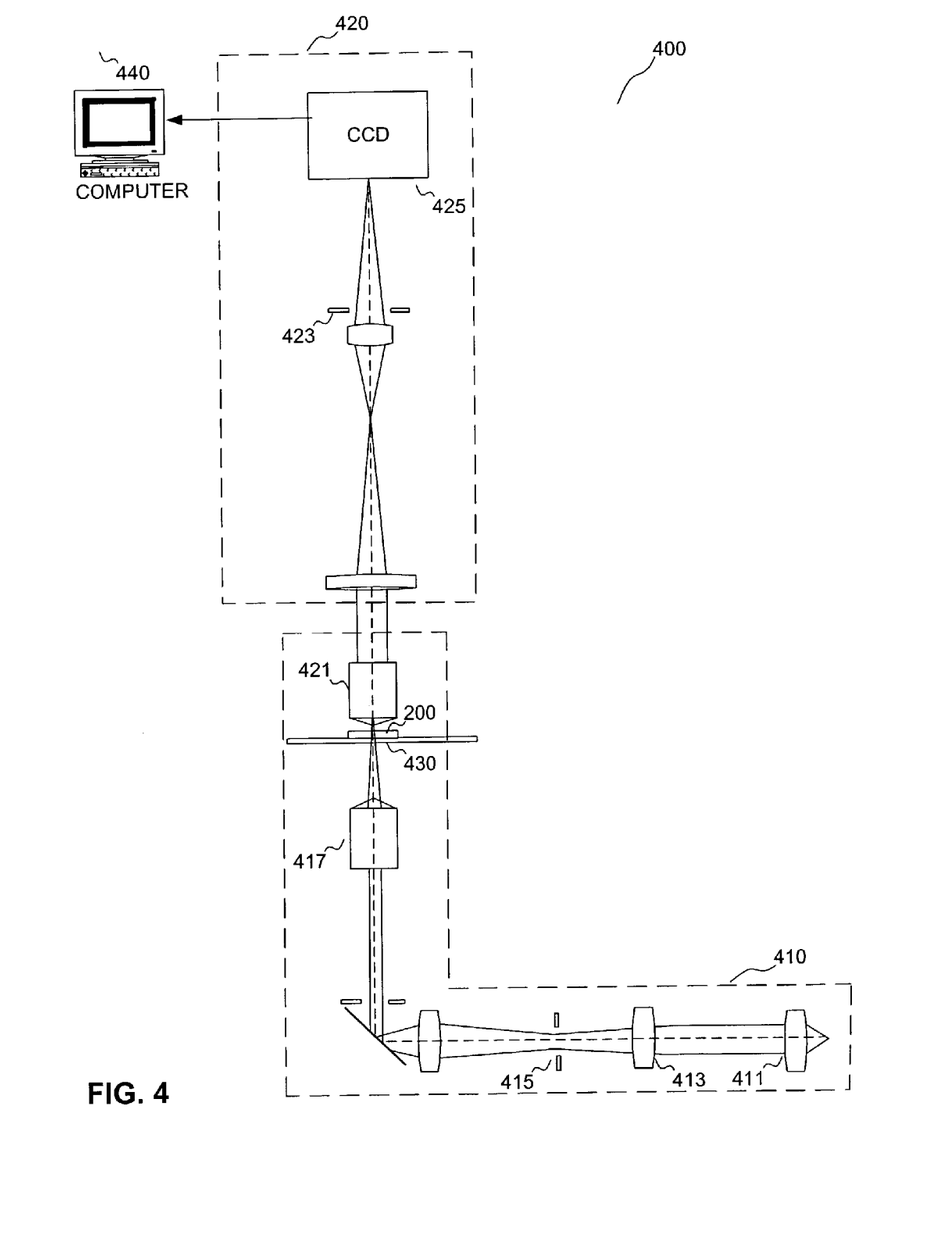
FIG. 4 is schematic diagram showing infrastructure of a conventional AIMS tool for detecting mask errors.

FIG. 4 is a schematic diagram of an AIMS tool. An AIMS tool 400 basically includes an illumination device 410 for projecting an incident light with a specific wavelength region, a microscope device 420 for detecting images formed on the mask, and a platform 430 positioned between the illumination device 410 and the microscope device 420. A mask (such as an AltPSM 200) is placed on the platform 430 for detection. The components in the tool are configured such that the illumination system 410 projects light from the back of the mask 200, and the microscope system 420 receives takes an image of the mask 200 from the front of the mask 200. The image of the mask 200 is then input to a computer software 440 for an analysis of mask quality.

The illumination device 420 includes an illumination source 411 for projecting at least a deep-UV light (365-, 248-, 193-nm or other wavelengths) and a narrow-band filter 413 for establishing a center wavelength (365-, 248-, 193-nm or other wavelengths) with a bandwidth of typically <10 nm FWHM. The coherence or "σ" of the light incident upon the mask 200 is adjustably controlled by a σ-aperture slider 415 positioned at a point in the base of the microscope device 420 conjugate with an objective lens 421 of the microscope device 420. The illumination device 410 further comprises a condenser lens 417 that focuses the light onto a small (submillimeter) region of the mask 200. The platform 430 can be moved up and down for an operator to select a through-focus image data of the mask 200. The microscope device 420 includes, in addition to the objective lens 421, at least a numerical aperture ("NA")-defining slider 423 for controlling the numerical aperture of the microscope 420 and a CCD camera for receiving the image data of the mask 200. The image data of the mask 200 is then outputted to computer software for analyzing the quality of the mask image to determine whether any mask defects exist and to measure the printability of the mask, etc.

AIMS tools are widely used for detecting the quality of photolithographic masks because the system can detect the quality of the mask before it is used in manufacturing semiconductor wafers. When the defects of a mask are detected, the mask can be discarded or repaired and then reevaluated by AIMS 400 for further detection. Alternatively, in some instances, the semiconductor manufacturing process can be adjusted to compensate for defects in the mask. In this manner, the quality of the semiconductor device can be effectively controlled and accordingly, the yield of the semiconductor device can be increased.

Although AIMS tools can effectively detect mask defects, use of such tools is very complex and expensive. Moreover, as AIMS tools are applied to detect larger areas of the mask, complicated software is required to calculate the mask patterns, thereby further increasing the cost of employing the AIMS system. However, for many masking manufacturing processes, it is not necessary to detect large areas of the mask and more particularly, to use expensive detection tools and complicated software to evaluate mask quality. A cheaper and simpler method and system for detecting the quality of the AltPSM are therefore needed.

SUMMARY OF THE INVENTION

The present invention provides an inexpensive and effective method and system for detecting aspects relating to the quality of an alternating phase shift mask.

One embodiment of the present invention provides a method for detecting errors in an alternating phase shift mask. The method comprises applying light incident upon an alternating phase shift mask at a plurality of different wavelengths, detecting output emitted from the mask resulting from applied incident light at each of the plurality of different wavelengths, and comparing the wavelength of applied incident light at which the detected output is at a minimum with a predetermined wavelength to detect imperfections in the mask.

Another embodiment of the present invention is to provide a system for detecting a quality of an alternating phase shift mask intended to operate at a predetermined wavelength. The system comprises a light source for illuminating light incident on the alternating phase shift mask and the incident light is of at least one wavelength, a detector for detecting output emitted from the mask when illuminated by the incident light, and a processor for associating detected results of the detector with a respective wavelength value of the incident light. In accordance with the embodiment, incident light at a plurality of wavelengths are applied, and the processor determines a wavelength value at which the detected output is at a minimum.

An additional embodiment of the present invention is to provide a method for detecting quality of an alternating phase shift mask, that includes a number of first phase shift areas respectively alternating with a number of second phase shift areas. The method comprises applying light incident at one side of the alternating phase shift mask at a plurality of different wavelengths, detecting output from the alternating phase shift mask when the alternating phase shift mask is scanned by the incident lights with different wavelengths, and comparing the output lights and incident lights to detect the quality of the phase shift mask.

In another embodiment of the present invention, the applied light is composed of a plurality of different wavelengths and the detector simultaneously detects output associated with each respective wavelength of incident light.

In another embodiment of the present invention, the detector detects an applied light composed of a plurality of different wavelengths in a sequential manner to individually detect output associated with each respective wavelength of the applied light.

BRIEF DESCRIPTION OF THE DRAWINGS

FIGS. 1A–1D are schematic diagrams illustrating a utilization of a conventional BIM in a photolithography process, in which:

FIG. 1A is a schematic diagram of the conventional BIM;

FIG. 1B is a phase distribution curve after a light passes through the BIM;

FIGS. 2A–2E are schematic diagrams showing a utilization of an AltPSM in a photolithography process, in which:

FIG. 2A is a schematic diagram of the AltPSM;

DETAILED DESCRIPTION OF THE PREFERRED EMBODIMENT

Hereinafter, preferred embodiments of the present invention will be described in detail with reference to the attached drawings. This invention may be embodied in many different forms and should not be construed as being limited to the embodiments set forth herein.

As described above, any imbalance in phase, transmission or CD in a photolithographic mask results in poor quality wafers after lithography via the mask. The present invention provides a method and system for detecting the phase and transmission balance of a mask such as an alternating phase shift mask.

In accordance with an embodiment of the present invention, any imbalance of phase and transmission of the mask is detected at the boundary between the 0-degree phase shift and 180-degree phase areas. This detects light intensity at the zeroth order to calculate whether there is any phase offset error occurring at the boundary. If the intensity of the zeroth order at a specific wavelength used in the lithography process is equal to zero, this indicates that there is no light diffraction occurring at the boundary. Therefore, a mask having zero light intensity at the zeroth order is considered to have no imbalance in the phase and transmission, and therefore can be used for patterning semiconductor devices in subsequent lithography processes. Otherwise, masks having any light intensity at the zeroth order at the specific wavelength may be sent back for repairs or discarded.

As is well known, an AltPSM is designed to operate at a specific wavelength. In currently available lithography technology, a light wavelength of 193 nm is used for patterning critical layers. Therefore, in an exemplary embodiment of the present invention, it is illustrated that the light intensity of the zeroth order at wavelength of 193 nm is equal to zero in order to obtain a good quality mask when applied in lithography with a light wavelength of 193 nm. The present invention, however, is not limited in the application of only 193 nm lithography, and instead can be easily applied at different wavelengths.

As a feature of an AltPSM, transmission of light decreases in the zeroth order in the region of operation, as shown in FIG. 2D. The transmission decrease is a function of both the incident wavelength and the phase offsets (i.e., the phase difference, for example, in the zeroth order, the phase difference is 180-degree in an ideal AltPSM structure). The phase difference is designed to optimize performance at the illumination wavelength. The property of reduced transmission can be used to quantify the amount of phase offsets by scanning the illuminating wavelength over an appropriate range. Furthermore, the location of the minima of the scanned illuminating wavelengths is related to the amount of phase error. Therefore, an embodiment of the present invention is to calculate phase error by scanning the incident wavelengths and identifying the minima of the relation curve of the incident wavelengths and the intensity of the zeroth order.

Figure 5:
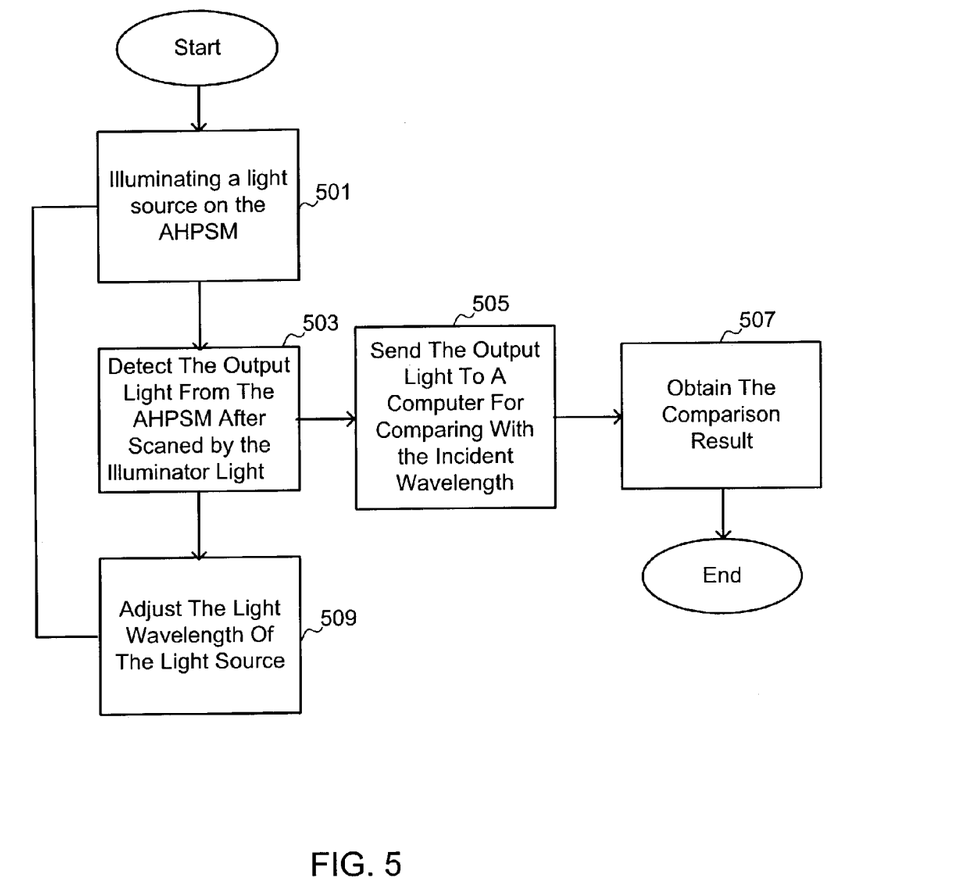
FIG. 5 is a flow chart illustrating a method for detecting the quality of an AltPSM in accordance with an embodiment of the present invention.

FIG. 5 is a flow diagram illustrating an exemplary method for detecting the quality of an AltPSM in accordance with an embodiment of the present invention. As shown at step 501, wavelength-adjustable incident light is illuminated on one side of the mask to be detected. Light output from the mask is detected in step 553. At step 505, the detected output light of the mask is sent to a computer for calculation. At step 507, the computer processes the detected light output in accordance with the applied incident light wavelength to obtain a calculation result. In accordance with one embodiment of the present invention, the calculation result may be a relation curve of the incident wavelength and the intensity of the zeroth order. At step 509, the wavelength of the incident light is adjusted and the adjusted incident wavelength are then utilized to scan the mask again. Therefore, the steps 501, 503, 505 and 507 are repeated several times to obtain various relation curves of the intensity of the zeroth order at different wavelengths.

In accordance with one embodiment of the present invention, the wavelength can be adjusted sequentially, such that the incident light is scanned (manually or automatically) on the mask at different light wavelengths. Alternatively, the incident light can be composed of a plurality of wavelengths. In this alternative embodiment, a detector used for detecting the incident light can be a CCD with multiple channels that can detect the different light wavelengths simultaneously, or a detector can be utilized that detects one wavelength at one time in a sequential manner.

Figure 6:
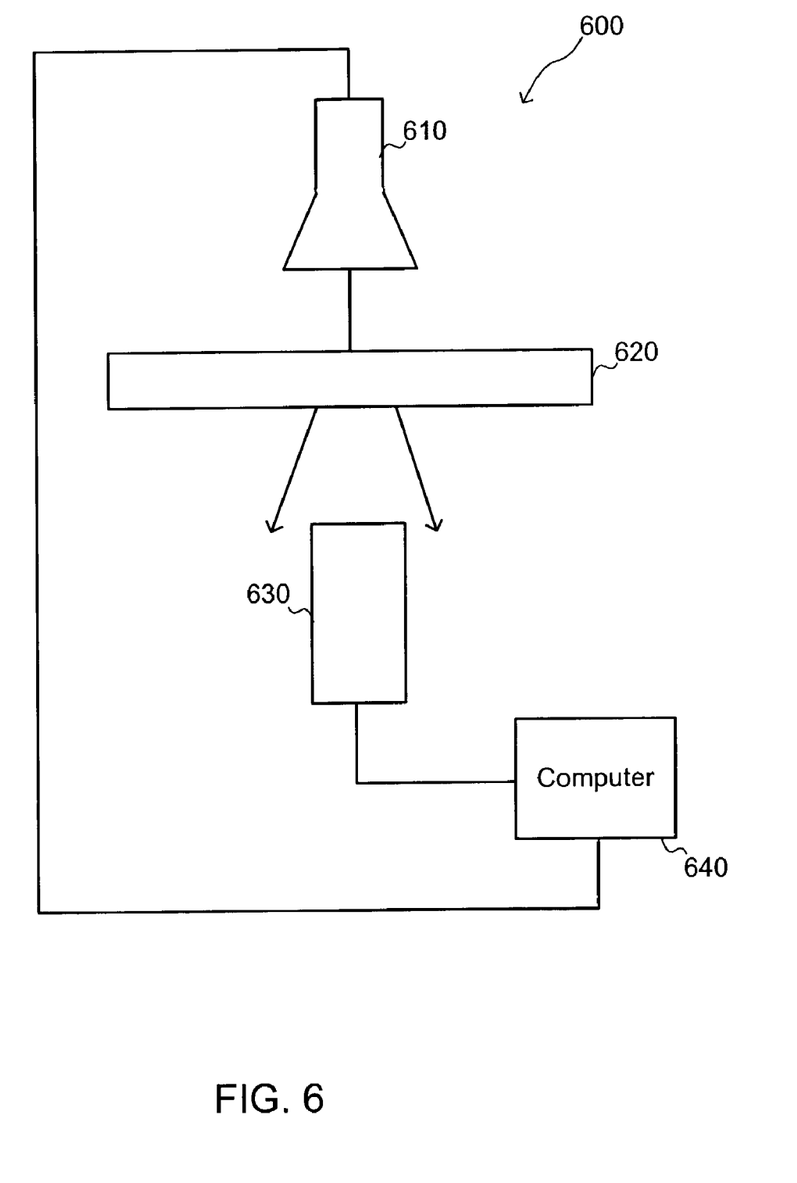
FIG. 6 is a schematic diagram showing a system for detecting the quality of an AltPSM in accordance with an embodiment of the present invention.

FIG. 6 is a schematic diagram of a system 600 for detecting the quality of an AltPSM in accordance with an embodiment of the present invention. The system of FIG. 6 can be applied in accordance with the method described above with reference to FIG. 5.

As shown in FIG. 6, system 600 includes at least one light source 610 illuminating an incident light on one face of a mask 620, such as an AltPSM, and a detector 530 that is located facing the opposite side of mask 620 for detecting the light output from mask 620. System 600 also includes a computer 640 for receiving the output light signals from detector 630 and calculating the light intensity of the output light signals based on the incident light wavelength of light source 610.

The wavelength of the incident light can be adjustable, such that detector 630 detects different output lights of mask 620 according to the incident lights of different wavelengths. Alternatively, the light source 610 can simultaneously illuminate a plurality of lights with a plurality of wavelengths incident on the mask 620. In accordance with this alternative embodiment, the detectors can be a CCD having multiple channels for detecting a plurality of wavelengths simultaneously, or the detector can be a filtered detector that detects a respective wavelength sequentially. In either case, the computer 640 gathers detected output light signal information and the associated incident light wavelength, and performs a calculation to obtain light intensity curves as shown in FIG. 7, which will be described in detail below.

According to an embodiment of the present invention, detector 630 is a detector apparatus which filters out light diffraction at orders other than the zeroth order, such that computer 640 only analyzes the light intensity of the zeroth order at different wavelengths. Accordingly, FIG. 7 only shows the relation curves of the incident wavelengths and the intensity of the zeroth order.

Figure 7:
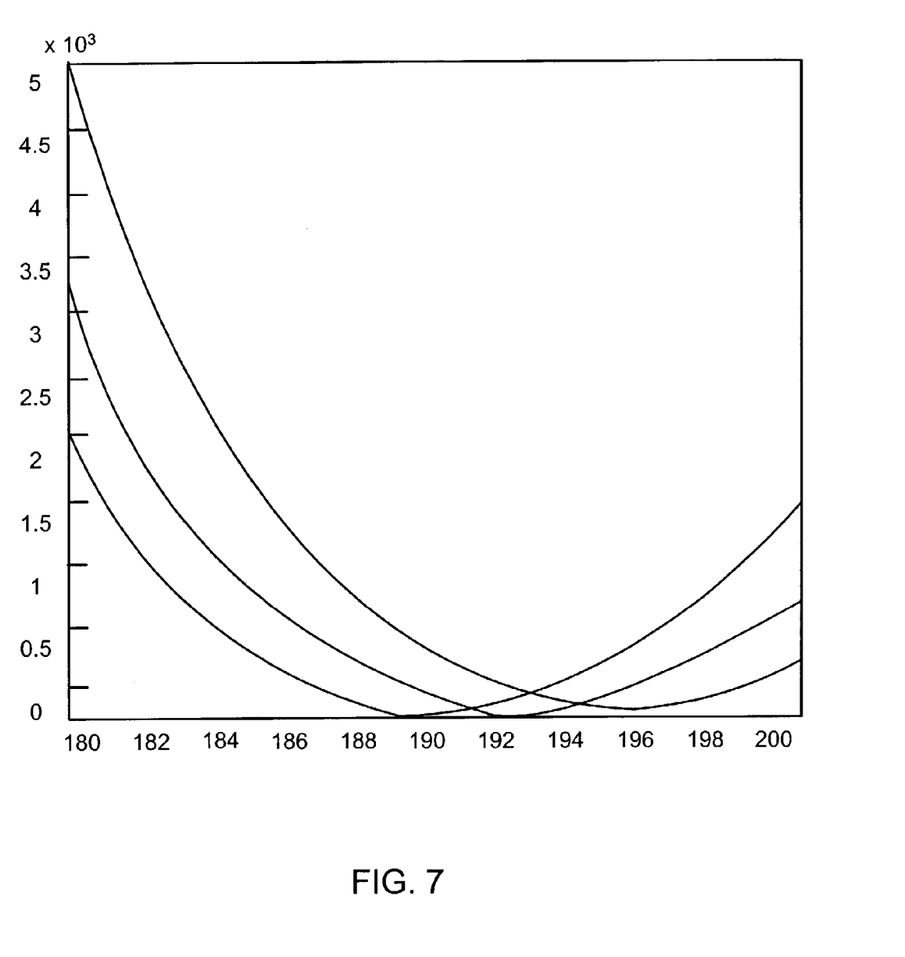
FIG. 7 is a graph showing a relation of incident wavelength to intensity of the zeroth order.

FIG. 7 shows various light intensity curves obtained by the method as described with reference to FIG. 5. As seen in this figure, the minima of the curve in the intensity of the zeroth order shifts as the phase difference is varied. Furthermore, the minimum of each curve corresponds to the incident wavelength when the intensity of the zeroth order is zero.

As shown, curve I has a minimum at 190 nm, curve II has a minimum at 193 nm and curve III has a minimum at 196 nm. As mentioned above, the location of the minima of each curve I, II and III is related to an amount of the phase error. Since the light wavelength used in the current photolithography technology is 193 nm, curve II, which has a minimum at 193 nm, indicates that the detected mask is an ideal mask with no phase or transmission error. This ideal mask will be used in the subsequent lithography technology for patterning the semiconductor substrate. Curves I and III, however, show that the incident wavelengths at the zeroth order have −3 nm and +3 nm errors, respectively, which mean that the detected masks may not have optimum performance at wavelength 193 nm. Those masks having the intensity curves as curves I and III, whose minimum of the intensity curve do not fall on the zero intensity point, may be discarded or repaired. Alternatively, a manufacturing process may be altered to accommodate the detected mask error.

Phase errors of the zeroth order can be also calculated by analyzing the relation curves of the wavelength and the intensity of FIG. 7. To more accurately obtain phase errors, a high-resolution monochronometer or monochronometer (not shown) may be utilized with the system of FIG. 6. In accordance with an embodiment of the present invention, the monochronometer may be used with the light source to adjust the wavelength of the incident light. Alternatively, a monochronometer can be utilized on either the front or the back side of the mask for a particular wavelength. In accordance with the present invention, the monochronometer may be a monochronometer which can be obtained from McPherson Co., model 2062, which is able to resolve down to 0.04 nm. Other instruments, such as an instrument, which has an even higher resolution, can be also used. By applying a high-resolution monochronometer, the scanning wavelength can be adjusted by a smaller difference each time. By scanning the fine-adjusted wavelength and by measuring the locations of the minima of the intensity of zeroth order curves, phase errors can be accurately calculated. The analysis result by the monochronometer is as shown in FIG. 8.

Figure 8:
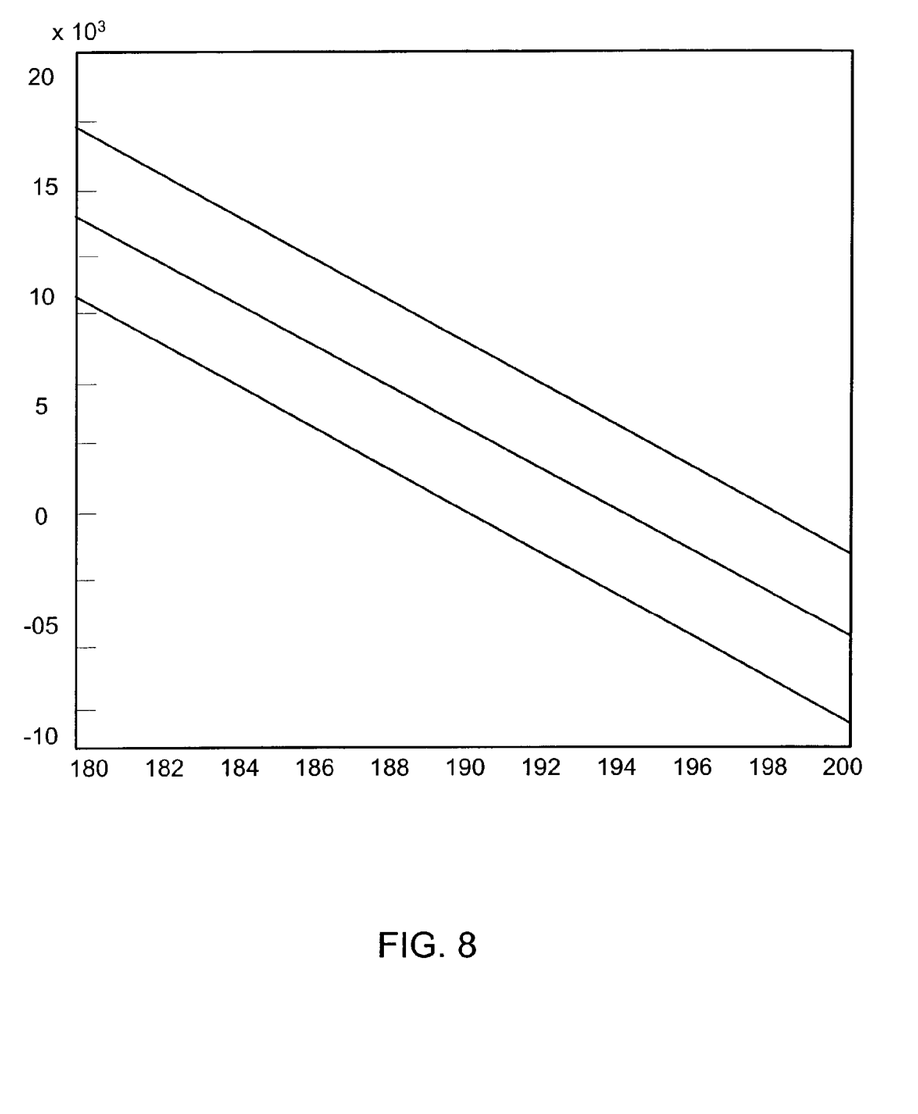
FIG. 8 is a graph showing a relation of incident wavelength to phase errors in a mask.

FIG. 8 shows relation curves of the incident wavelengths and the phase errors. As shown in curve B has a zero phase error when the incident light wavelength is 193 nm. That is, the detected mask with curve B is an ideal mask and will be used in subsequent photolithography processes. The remaining, curves A and C, have zero phase errors at incident light wavelengths 190 nm and 196 nm, respectively, indicating that curve A has −3 nm phase error and curve C has a +3 nm phase error. The masks corresponding to curve A and C, therefore, will be discarded, repaired, or utilized in a manufacturing process that compensates for the detected mask error.

Accordingly, the system and method of the present invention determines the quality of the mask by scanning the wavelength-adjustable incident light on the detected mask and measuring the minimum of the curve of the light intensity of the zeroth order, as represented by the curves of FIG. 7. The system and method of the present invention can also determine the phase errors of the detected mask by detecting the output light from the detected mask and comparing the output light wavelength with the incident wavelength, as represented by the curves of FIG. 8.

The present invention provides an uncomplicated, and inexpensive quick system and method for determining the phase shift offsets in an AltPSM. No complex and expensive assembly of the components in the system of the present invention is required, in contrast with systems that are presently widely used, such as AIMS tools. For example, according to an embodiment of the present invention, light source 510 for illuminating incident light can be chosen from those that are already available in the market, as long as it is sensitive to the 193 nm wavelength. The detectors can be any type of detectors, such as those which can filter out light diffraction of other orders than the zeroth order. The present invention can include a collimator under the light source to provide incoherent incident lights. The mask can also be added with an anti-reflection coating in order to obtain a better performance. As mentioned earlier, the system may include a high-resolution monochronometer on the front or the back side of the mask to be detected to finely adjust the wavelength of the incident light.

Furthermore, the present invention may be used for detecting a small area of the mask to achieve an idea regarding the local variation in the phase etched performance. For a larger mask, the detection method of the present invention can be carried out with a small collimated light beam on different locations of the mask. By detecting the phase offsets at the boundaries between the 0-degree phase shift and 180-degree phase shift areas in the small area of the mask, the quality of a local area of the mask can be estimated accordingly.

In addition to the applicability to simple 1D array like patterns on the semiconductor substrate, the method in accordance with the present invention can also easily be extended to 2D patterns. In addition, by incorporating some sophistication in the inspection/characterization tool, it is possible to extend this method to an arbitrary layout, where the magnitude of the DC component is characterized via, for example, a simulation and then measured.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method for detecting errors in an alternating phase shift mask, comprising:
   applying light incident upon an alternating phase shift mask at a plurality of different wavelengths;
   detecting output emitted from the mask resulting from applied incident light at each of the plurality of different incident wavelengths; and
   comparing the wavelength of applied incident light at which the detected output is at a minimum with a predetermined wavelength to detect imperfections in the mask.

2. The method of claim 1, wherein wavelength adjustable light is scanned in a sequential manner across the plurality of different wavelengths incident to the mask.

3. The method of claim 1, wherein the applied light is composed of the plurality of different wavelengths, and the detector simultaneously detects output associated with each respective wavelength of incident light.

4. The method of claim 1, wherein the applied light is composed of the plurality of different wavelengths, and the detector detects the applied light in a sequential manner to individually detect the output associated with each respective wavelength of incident light.

5. The method of claim 1, wherein the detected output represents an intensity of emitted light occurring at boundaries between phase shift areas on the mask at each different wavelength of applied incident light.

6. The method of claim 5, wherein detected output is light diffraction of a zeroth order.

7. The method of claim 2, wherein the mask is scanned at a plurality of wavelengths ranging from below to above the predetermined wavelength, and the detected output is a curve according to a function of the applied incident wavelength having a single minimum.

8. The method of claim 1, further comprising the step of calculating the difference between the wavelength of applied incident light at which the detected output is at a minimum and the predetermined wavelength to determine an amount of phase error.

9. A system for detecting a quality of an alternating phase shift mask intended to operate at a predetermined wavelength, comprising;
   a light source for illuminating light incident on the alternating phase shift mask, wherein the incident light is of at least one wavelength;
   a detector for detecting output emitted from the mask when illuminated by the incident light, wherein a difference between the wavelength of the incident light at which the detected output is at a minimum and the predetermined wavelength is a phase error associated with the mask; and
   a processor for associating detected results of the detector with a respective wavelength value of the incident light, wherein incident light at a plurality of wavelengths are applied, and the processor determines a wavelength value at which the detected output is at a minimum.

10. The system of claim 9, wherein the applied light is composed of a plurality of different wavelengths, and the detector simultaneously detects output associated with each respective wavelength of incident light.

11. The system of claim 9, wherein the light source is adjusted to progressively illuminate the mask at different wavelengths ranging below and above the predetermined wavelength.

12. The system of claim 9, wherein the detector detects light diffractions occurring on boundaries between 0-degree and 180-degree phase shift areas on the mask.

13. The system of claim 12, wherein the light diffractions occurring on the boundaries correspond to a light intensity of a zeroth order.

14. The system of claim 9, wherein the predetermined wavelength is 193 nm.

* * * * *